United States Patent [19]

Laue

[11] 4,020,678

[45] May 3, 1977

[54] METHOD AND SYSTEM FOR TESTING OF INDIVIDUAL GEAR TEETH

[76] Inventor: Günter Laue, Petristr. 26, 4920 Lemgo 1, Germany

[22] Filed: Jan. 14, 1976

[21] Appl. No.: 649,097

[52] U.S. Cl. .................................. 73/67.2; 73/162
[51] Int. Cl.² ......................................... G01M 7/00
[58] Field of Search ................. 73/67.1, 67.2, 67.4, 73/162

[56] References Cited

UNITED STATES PATENTS

| | | | |
|---|---|---|---|
| 3,320,796 | 5/1967 | Darby | 73/67.1 |
| 3,623,358 | 11/1971 | Sugimoto | 73/67.2 |

FOREIGN PATENTS OR APPLICATIONS 1,056,088  1/1967  United Kingdom ................ 73/67.1

*Primary Examiner*—S. Clement Swisher
*Attorney, Agent, or Firm*—Michael J. Striker

[57] ABSTRACT

A previously charged capacitor is discharged through a coil having a core situated in the vicinity of the steel tooth. The discharge creates a surge of magnetic circulation whose attractive forces cause a bending of the steel tooth which then executes flexural vibrations. A sensor senses the flexural vibrations and furnishes an electrical signal whose amplitude and/or frequency characteristics are examined to detect defects in the tooth.

17 Claims, 6 Drawing Figures

METHOD AND SYSTEM FOR TESTING OF INDIVIDUAL GEAR TEETH

BACKGROUND OF THE INVENTION

The present invention relates to a method and system for testing the bending resistance and damping of individual gear teeth made of steel in order to determine the presence of defects. In particular it relates to such methods and systems wherein the sudden application of a force causes the tooth to undergo free flexural vibrations.

In order to judge the condition of highly-loaded gears at the beginning and during their operating life, a non-destructive testing procedure is required in order to detect defects in the material, small cracks at the base of the tooth and the beginning of defects resulting from metal fatigue at the surface of the tooth, before damage or complete destruction can occur.

For objects which have an audible characteristic vibratory frequency, a subjective testing of such errors is a well-known procedure. The procedure consists of transferring a sudden pulse of energy to the object by an impact and then deriving information concerning possible defects from the resulting vibrations and, in particularly, from the frequency spectrum (tone) and the attenuation of the oscillations (damping). This simple method cannot be applied to the testing of individual gear teeth for the following reasons:

The frequency of the characteristic flexural vibrations of a tooth are in the ultrasonic region and therefore not audible; and the time during which the force is applied, for example if the force of a hammer is applied to a tooth, comprises a multiple of the period of the characteristic vibratory frequency of a tooth, so that the applied energy cannot be efficiently converted into vibratory energy. It is required that the time duration of application of the force to the tooth be at the most equal to approximately one-half of the characteristic vibratory cycle of the tooth.

Objective methods of determining the frequency and damping of the exponentially decreasing vibration or oscillation in response to a transient impact are known which are utilized when the accuracy requirement and/or the frequency do not allow a subjective evaluation. These methods and system utilize an electrical sensor which furnishes an electrical signal corresponding to the deformation of a freely vibrating system to an electronic evaluation circuit; the force is, however, still applied by mechanical means and for an impact duration which is too long for use in the evaluation of gear teeth.

In order to be able to carry out a damping measurement in accordance with the decay of vibrations in those cases when the characteristic frequency or vibration of the test sample, as for example the gear tooth, lies in the ultrasonic region, a method and system is known and published in the journal Messen and Prufen/Automatik, 1973, Heft July/August S. 478 and Heft September S. 575) wherein the test sample is continuously energized at a frequency corresponding to its characteristic frequency of vibration and the energy supply is then abruptly cut off. Free, approximately exponentially decreasing oscillations then occur which can be readily evaluated. The transfer of vibratory energy to the test sample may take place by means of forces created in a magnetic field which is generated by an alternating circulation induced in a coil, the coil being connected as part of an oscillator tuned to the characteristic frequency of the test sample. However, this measuring process is of course made very difficult because the characteristic frequency must first be known. Further, the resonant increase of the vibration varies greatly as a function of the damping and requires that, for each tooth, an adjustment of the oscillator output must be made of a constant sensitivity is to be maintained.

SUMMARY OF THE INVENTION

It is an object of the present invention to furnish a system and method in which a non-destructive testing of steel test sample may take place even for test samples whose characteristic vibratory frequency lies in the ultrasonic region in particular gear teeth made of steel, are to be suddenly subjected to a force in order to create flexural vibrations whose decay characteristics result in a readily readable indication or display. Further, it should be possible to carry out the testing by means of portable equipment without removing the gears whose teeth are to be tested from the equipment wherein they operate.

The present invention is a method for non-destructive testing of the tooth of a steel gear which comprises the steps of creating a surge of magnetic circulation in a coil positioned in the proximity of the tooth thereby applying a pulsed magnetic force to the tooth which induces free flexural vibrations therein. The flexural vibrations are sensed and an electrical signal is furnished corresponding thereto. The electrical signal is then evaluated as to amplitude and/or frequency in order to determine the presence of possible defects.

In accordance with a preferred embodiment of the present invention, the surge of magnetic circulation is created periodically at a frequency corresponding to the frequency of the source of electrical energy or an integral multiple or submultiple thereof.

In accordance with the system of the present invention means are provided for applying a pulsed magnetic force to the steel tooth, thereby creating free flexural vibrations therein. Sensor means are provided for sensing said free flexural vibrations and furnishing a corresponding electrical signal. In a preferred embodiment of the present invention the pulsed magnetic force is created by the discharge of a capacitor through a coil. The coil is either directly connected to the capacitor by means of a switch or is connected to the secondary winding of a transformer whose primary winding receives the discharge of the capacitor.

In a preferred embodiment of the present invention the resonant frequency of the oscillator circuit including the capacitor being discharged and the inductivity of the coil is approximately equal to the flexural vibration frequency of the tooth or exceeds this frequency.

In a further preferred embodiment of the present invention the discharge of the capacitor is initiated by the switching of an electronic switch, preferably a thyristor, from the nonconductive to the conductive state in response to a switching signal, means being provided to furnish said switching signal in a predetermined time relationship with, or in response to the discharge of said capacitor.

In a further preferred embodiment of the present invention the sensor means are contactless sensors which furnish an electrical signal corresponding to the variation as a function of time of the deflection of the flank of the tooth or a derivative with respect to time thereof. In a further preferred embodiment of the present invention the electrical signal is displayed on an oscilliscope whose horizontal deflection time does not exceed approximately five times the time of the tooth vibrations. In a further preferred embodiment of the present invention, the coil, the iron core associated with the coil and the sensor are all arranged within a yoke which has a handle, the yoke further having a number of conforming surfaces which conform to the tooth surface of the tooth adjacent to the tooth under test.

In a further preferred embodiment, drive means are provided which drive the yoke in a direction radial with respect to the gear, while the gear is rotated by an angle of rotation corresponding to the angular distance between two adjacent teeth.

In a further preferred embodiment of the present invention, the invention is a part of standard gear measuring apparatus which determines errors in the shape and angular distribution of the teeth around the gear.

The advantages achieved by the present invention include the following:

First, defects in the material, small cracks at the base of the tooth and beginning cracks resulting from metal fatigue at the tooth surface can be readily detected at an early stage and with great reliability. In most cases, the gear must not be removed from the equipment wherein it operates for testing purposes. The test apparatus is portable. The energy utilized is sufficiently small that the energy supply can be derived from a portable accumulator. The peak value attained in the first half period of the free flexural vibrations is practically independent of the damping of the tooth and the sensitivity therefore remains relatively constant without adjustment or regulation.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

Figure 1:
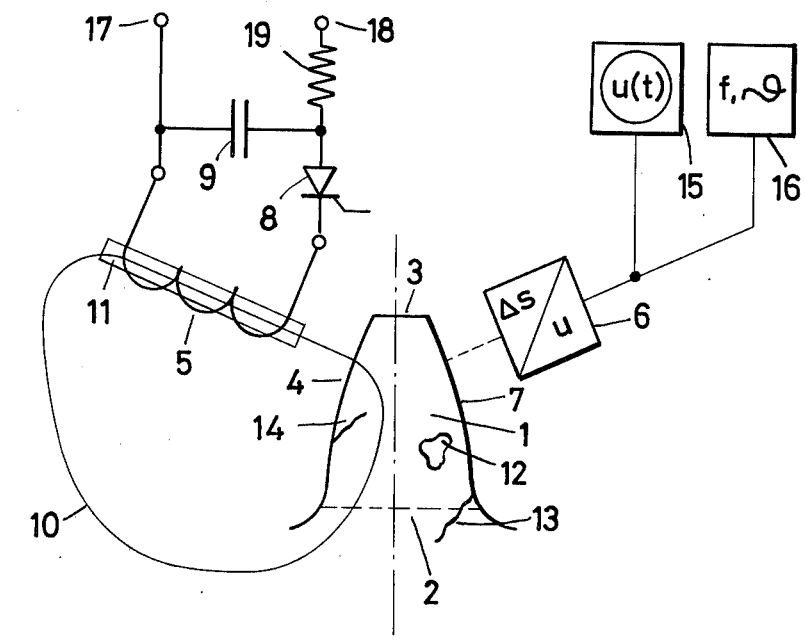
FIG. 1 shows an individual tooth of a gear wheel with the coil, the capacitor, and an electrical sensor and indicator arrangement.

DESCRIPTION OF THE PREFERRED EMBODIMENTS:

A preferred embodiment of the present invention will now be described with reference to the drawing.

The individual tooth 1 of a gear can be considered as a beam restrained at one end and able to execute bending or flexural vibrations. The fixed end of the beam is the root of the tooth 2, the gear being considered a rigid body. The free end of the beam is the addendum 3. The axis of coil 5 is positioned approximately perpendicular to the tooth flank 4, while the electrical sensor 6 is mounted opposite the other flank 7. This arrangement of positioning relative to two different flanks of the tooth was chosen for clarity of presentation and is preferable for constructive reasons. It is of course possible that the sensor 6 is also mounted opposite flank 4.

The sensors for sensing the deflection of the tooth are commercially available and include capacitive sensors, inductive sensors, accoustic sensors, pneumatic sensors and optoelectronic sensors. In capacitive sensors the change in the position of the tooth relative to the sensor causes a change in a capacitance which in turn changes the capacitive reactance of, for example, a tuned oscillator. In an inductive sensor, as for example furnished by the Kaman Sciences Corporation in the United States, the deflection movement causes a damping of the eddy current in a high frequency oscillator circuit. In optoelectronic sensors the flank of the tooth reflects a light beam which then is impinged upon a photoreceiver whose resistance, for example, varies as a function of the light impinging thereon. Such a sensor is furnished by the United Detector Technology Inc. of the United States. Such sensors are readily available commercially and need not be further discussed here. In general contactless sensors such as the above-described sensors are preferred but of course Piezo electric sensors could also be utilized.

Figure 4:
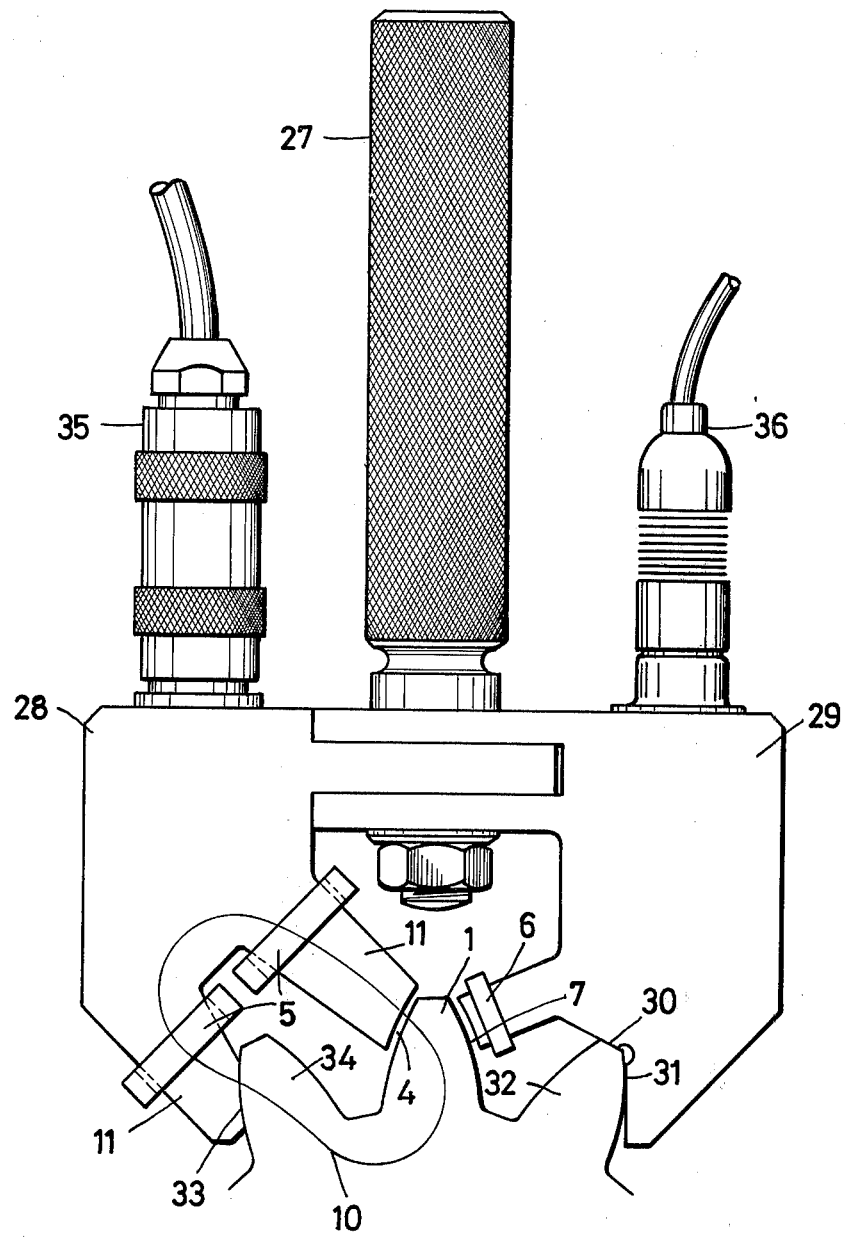
FIG. 4 shows a yoke including the coil, iron core, and sensor.

Also shown in FIG. 1 is the circuit for creating the surge of magnetic circulation in coil 5. This comprises a capacitor 9 and a thyristor 8 as well as a resistor between the capacitor and the voltage applied at terminals 17 and 18. A circuit for charging the capacitor and then discharging same through a thyristor is shown in FIG. 4 and will not be discussed in detail at this point. However, after the thyristor 8 has switched from the blocked to the conductive state, the previously charged capacitor 9 having a capacitance $C_E$ discharges through coil 5 which has an inductivity $L_E$. The discharge current is effective in creating a surge of circulation (magnetic potential) which in turn generates a magnetic field indicated by a line 10 in FIG. 1. If the permeability in the flux path is assumed to be constant, magnetic attractive forces are created in the air gap which increase as a square of the circulation.

The losses in coil 5 and capacitor 9 are sufficiently small that, in the absence of thyristor 8, the discharge current would result in a series of oscillations which change direction approximately every half period of the resonant frequency $f_E = \frac{1}{2}\pi \sqrt{L_E.C_E}$. However thyristor 8 allows current to pass in one direction only and blocks current in the other direction. Thus a discharge current flows through coil 5 only during the first half period. The length of time during which the discharge current exists and therefore the length of time during which the pulsed magnetic force is applied to the tooth is inversely proportional to the resonant frequency $f_E$. Thyristor 8 of course is not retriggered immediately. Thus by a suitable choice of values of $L_E$ and $C_E$, the time of application of the force can be held to a sufficiently short time interval. The arrangement can be further modified by interconnecting a transformer between the capacitor and the coil, thereby creating additional variables for creating the appropriate time duration of application of force to the tooth.

Tooth 1 is deflected during the surge of the magnetic force of attraction and therefore a portion at least of the surge energy is transferred to tooth 1. Tooth 1 in turn, if not excessively damped, undergoes substantially exponentially decreasing bending vibrations or oscillations. This process is, strictly speaking no longer periodic. However, in general, one also speaks here of a period and understands by period the basic harmonic characteristic oscillation whose characteristic frequency $f_B$ is equal to $$f_B = \tfrac{1}{2}\pi \sqrt{m/c}$$

where the bending resistance $c = 3EI/l^3$; the modulus of elasticity is $E$; the surface moment of inertia is $I$; and the length of the beam is $l$; and it is assumed that the beam is a beam fixed at one side and having a point mass $m$ at its other extremity.

For constant point mass $m$, knowledge of the characteristic frequency $f_B$ thus allows variation of the bending resistance $c$. Similar relationships exist in the actual tooth 1 having a distributed mass and variable surface moment of inertia. Under those conditions the characteristic frequency $f_B$ can be found only after relatively complicated theoretical calculations and depends among other things heavily on the module of the gear. For a module of 10 the characteristic frequency is approximately 30 kHz, for a module of 3 it is approximately 80 kHz.

Thus during the time of the surge two oscillatory systems, one electrical and one mechanical are mutually coupled by means of the magnetic field, but with a time limitation determined by thyristor 8. The energy which at the beginning is stored in the electrical system is transferred without loss to the mechanical system which has no energy at the beginning but which is free to oscillate, only if $f_B$ is equal to or less than $f_E$, that is when the duration of the surge is less than one-half period of the characteristic oscillation of tooth 1.

The above-computed characteristic frequency $f_B$ for bending oscillations of a beam which is fixed on one side, and is massless but has a point mass at its end and corresponding oscillations of the tooth will occur under practical conditions only if sufficient homogeneity exists. Deviations from homogeneity as for example a cavity or shrink hole 12, a crack 13 or small pitting or hole 14 (which signals a fatigue failure) affect the stress distribution and change, among other things, the surface moment of inertia I and thereby the bending resistance $c$ and the characteristic frequency $f_B$. Further, at the cracks, additional friction damping occurs which causes a faster conversion of the vibratory energy into heat and therefore causes the oscillations to be damped in a much shorter time. The envelope of the oscillations as a function of time may be described in a good approximation by e-curve $k \cdot e^{-t/T_A}$, having a constant $k$ and a time constant $T_A$. The characteristic frequency $f_B$ as well as the time constant (damping time) $T_A$ or dependent characteristics can be derived from the picture on oscilloscope 15 and/or another oscillation analyzer 16. Other generally known parameters for the damping process can be computed as follows if it is assumed that $T_A$ is much greater than $1/f_B$:

$$T_A = 1/\delta_A = \tfrac{1}{2}\pi f_B \Theta = 1/f_B \Lambda = Q/\pi f_B$$

where the damping constant is $\delta_A$; the damping degree is $\Theta$; the logarithmic decrement is $\Lambda$ and the figure of merit of the oscillatory circuit is $Q$. ($Q$ being the figure of merit of a corresponding electrical oscillatory circuit.)

The measurements results of the individual teeth of a gear are judged relative to deviations from desired or reference values. These reference values may for example be the average values $f_B$ and $T_A$ derived from a first testing of a gear and representing the average values derived from all the teeth of said gear or, alternatively, for the testing of new gears particular quality requirements are taken into consideration. Within limits, it is possible to determine the type of defect by the particular deviation. For example for cavities 12 the deviation in $f_B$ is stronger than that in $T_A$, while for cracks 13, 14 the defects cause a larger deviation in $T_A$ than in $f_B$.

Capacitor 9 is charged by means of a voltage source which is not shown and which is connected to terminals 17, 18. the charging process takes place over a limiting resistor (19 in FIG. 1, R in FIG. 5) only when the applied AC voltage has the correct polarity relative to thyristor 8. As will be described in greater detail with reference to the circuit in FIG. 5, it is not necessary that the AC voltage first be rectified. Thyristor 8 can be switched to the conductive state near the positive peak values of the alternating voltage which occurs in the middle of each positive half period. However the switch-in time of the thyristor must be maintained sufficiently exactly relative to the zero passage of the applied AC voltage in order that, for example oscilloscope 15, will have a stationary picture. This direct application of the AC voltage to the circuit is possible since the tooth, which has been activated by means of the surge of forces oscillates in a time period which is small relative to the half period of the applied AC voltage.

The preferred embodiment of a circuit for charging and discharging the capacitor (9 in FIG. 1, C in FIG. 5) will now be described with reference to FIG. 5. The AC voltage is applied at terminals 17 and 18. The voltage by means of which capacitor C is charged through the resistor R which may be adjusted to effect the desired charging time constant, is maintained constant by a Zener diode Dz. The voltage across capacitor C is applied to the control electrode of a unijunction transistor P. As soon as it reaches a predetermined value as determined by the base resistors of the unijunction transistor $R_{B1}$, $R_{B2}$ the unijunction transistor switches to its low ohmic state and causes capacitor C to discharge through resistance $R_{B1}$ and the gate-cathode circuit of a thyristor denoted by T in FIG. 5 and corresponding to thyristor 8 of FIG. 1.

Figure 2:
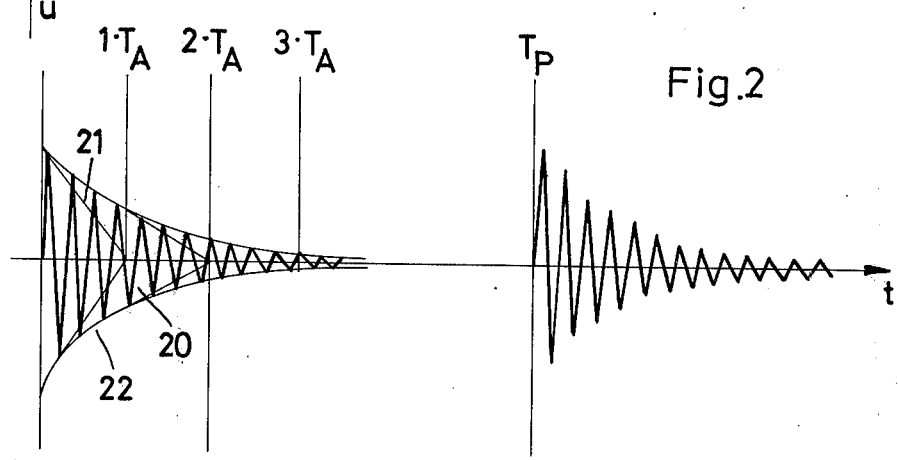
FIG. 2 shows two substantially exponentially decaying oscillations or vibrations of a tooth for a linear ordinate scale.
Figure 3:
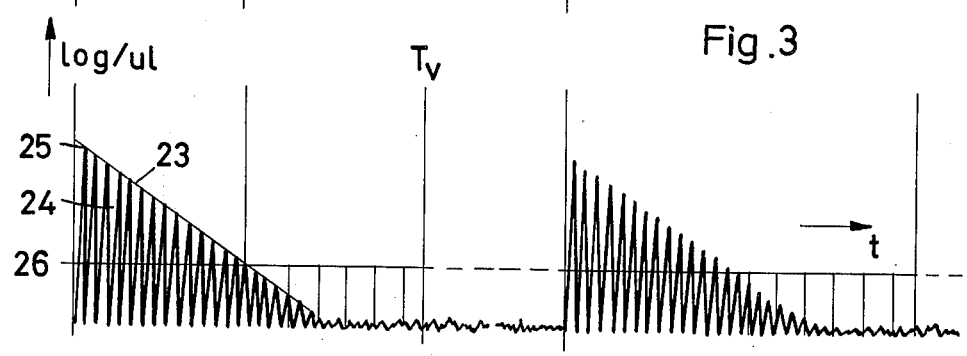
FIG. 3 shows two approximately exponentially decaying oscillations or vibrations of a tooth after rectification and for logarithmic ordinate scale.
Figure 5:
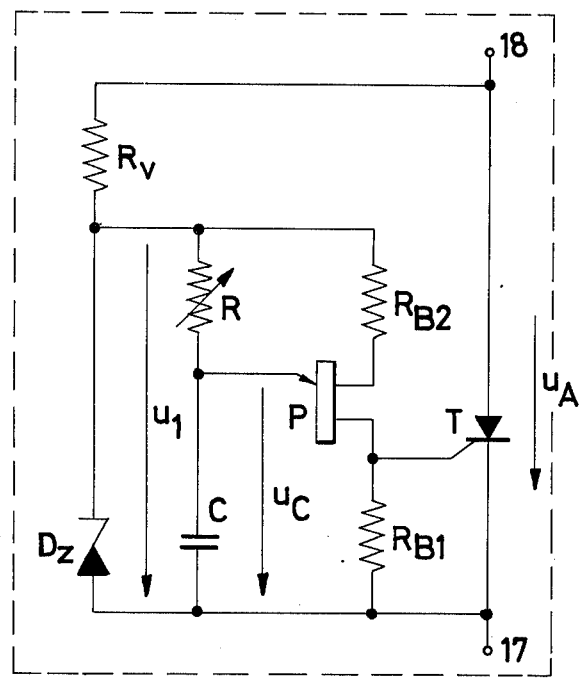
FIG. 5 shows a circuit for charging the capacitor and discharging the same through a coil.

If the circuit of FIG. 5, or an equivalent circuit is used to charge capacitor C, the resulting voltage furnished by sensor 6 which may be viewed on oscilloscope 15 is indicated by curve 20 of FIG. 2. Both the voltage axis ($u$) and the time axis ($t$) are linearly divided in this case. The voltage is proportional to the output voltage of sensor 6 and thereby to the deflection $\Delta s$ of the tooth flank 7 in the example shown; however of course either the first or second derivative with respect to time of the deflection $\Delta s$ may be utilized without change in the determination of the characteristic frequency $f_B$ and the damping time $T_A$. The characteristic frequency $f_B$ is derived from the number of times that curve 20 passes through the $t$ axis in a suitably chosen time interval. The decay time $T_A$ is the point on the $t$ axis through which a line 21 which is tangent to the $e$ function envelope 22 at its origin passes. The peak values of the voltage $u$ have decreased to less than 1% of their starting value after a time of $5 \cdot T_A$ so that a new application of force to tooth 1 following this time is appropriate. The time is denoted by $T_p$ in FIGS. 2 and 3. When the voltage applied to terminals 17 and 18 is a DC voltage, the time $T_p$ can be chosen without much restraint, while the time $t_p$ during the charging of the capacitor from an AC source is fixed by the periodicity of the latter.

The construction of the tangent 21 at the origin of the $e$ function envelope can be avoided in accordance with the present invention by picturing the time varying rectified output voltage of sensor 6 or the magnitude $u$ of the voltage proportional thereto on a logarithmic scale log $u$, with a linear time deflection. Then an approximately straight line 23 results as the envelope of the peak values 24 of one polarity. The slope of this straight line is proportional to $1/T_A$.

The following method may also be used advantageously to derive the value $T_A$:

First, the first peak value 25 of the time varying oscillations 24 is held constant; a rectangular variable reference voltage is generated and is pictured on the oscilloscope, the peak value of this voltage (26) being constant and a predetermined fraction, e.g. $1/(2e)=0.1353$ of the peak value 25; the distance 25/26 on the screen of the oscilloscope 15 is kept constant (calibration of the amplification factor); the deflection time is calibrated by means of a raster division or such like and time $2T_A$ is read at which the lines 23 and 26 intersect. This is correct since the peak values 24 decrease to a value of $1/(2e)$ within a time $2T_A$. Of course other fractions may be used in a similar fashion.

The accuracy of reading the time $2T_A$ is increased if, in particular, for direct energization from an AC source, the delay in the time deflection between times $T_V$ and $T_p$ is utilized in accordance with the present invention so that the oscillations of interest may be pictured in as large a form as possible on the screen of oscilloscope 15. The peak values 26 of the reference voltage are chosen in such a manner that any noise voltage can have no effect on the reading. In the examples shown, the noise voltages may go as high as 5% of the first peak value 25 without influencing the results. When a logarithmic representation of the time varying, rectified output voltage of sensor 6 or the voltage u proportional thereto is utilized, the characteristic frequency $f_B$ is derived from half the number of peaks in a positive direction within a suitably chosen time interval.

As shown in FIG. 4, in a preferred embodiment of the present invention coil 5, sensor 6 and iron core 11 with return flux path are all arranged in a yoke 28, 29 having a handle 27. The portion 28 of yoke 28, 29 is made of a magnetizable material. The measuring portion 29 is made of an unmagnetizable material and, in the embodiment shown, has two surfaces 30, 31 which conform to the corresponding surface of a neighboring tooth 32. A point or a line contact is sufficient. However, the transfer surface 33 between iron core 11 and the other neighboring tooth 34 must conform as much as possible in order that the amount of magnetic potential required for this junction is as little as possible. The other junction relative to flank 4 of the tooth under test must however contain an air gap in order that tooth 1 may vibrate freely. The connection to thyristor 8 and to capacitor 9 takes place over a terminal 35, while the connection to oscilloscope 15 and to whatever other analyzer for the oscillating parameters is present over a terminal 36.

Figure 6:
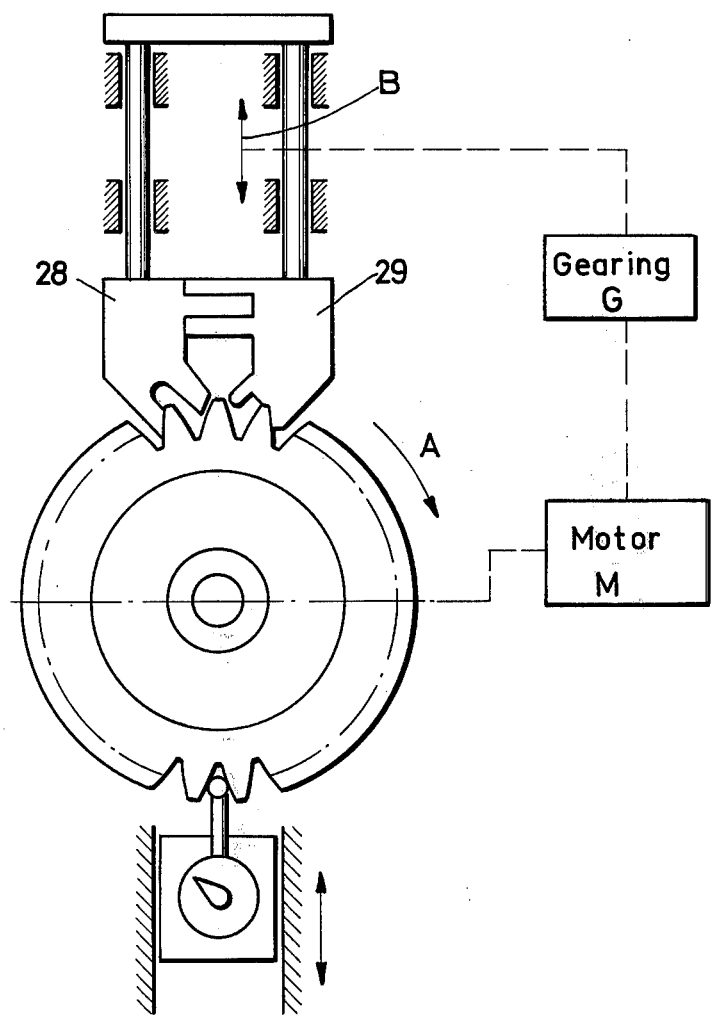
FIG. 6 shows the present invention incorporated in standard gear test apparatus.

In most cases, the teeth of the gear may be tested without removing them from their equipment, that is, after opening of the gear cover, etc. by means of yoke 28, 29 which is applied thereto by hand. However, if the testing process is to be made automatic as in a preferred embodiment of the present invention, the gear must be clamped down, an arrangement as shown in FIG. 6 is utilized. Drive means including a motor M and gearing G drive the yoke 28, 29 in a substantially radial direction as indicated by arrow B as the gear is rotated in the direction denoted by arrows A from one tooth to the next. Also as indicated in FIG. 6, the testing in accordance with the present invention and utilizing yoke 28, 29 may be combined with standard gear testing by mounting the system of the present invention relative to the standard gear test apparatus as also indicated in FIG. 6. Under these conditions, the time for mounting and unmounting the gear in the test fixture is required only once both for the standard gear test apparatus and for the test apparatus in accordance with the present invention.

While the invention has been illustrated and described as embodied in specific apparatus for applying a magnetic attractive force to the tooth under test, it is not intended to be limited to the details shown, since various modifications and circuit changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. System for testing the bending resistance and damping of an individual tooth of a steel gear for detecting defects therein, comprising, in combination, means for creating a pulsed magnetic attractive force for bending said tooth and causing said tooth to execute free flexural vibrations; and sensing means positioned in operative proximity to said tooth for sensing said flexural vibrations and furnishing an electrical signal having a predetermined characteristic varying in correspondence thereto, wherein said means for creating a pulsed magnetic attractive force comprise a capacitor, means for charging said capacitor to a predetermined voltage, a coil, and switch means interconnected between said capacitor and said coil for discharging said capacitor through said coil, thereby creating a surge of magnetic circulation in said coil.

2. A system as set forth in claim 16, further comprising a transformer interconnected between said capacitor and said coil, said transformer having a primary winding connected to said capacitor and said switch for receiving the discharge current of said capacitor, and a secondary winding connected to said coil.

3. A system as set forth in claim 1, wherein said capacitor and said coil form a resonant circuit having a resonant frequency $f_E$; wherein said tooth has a characteristic flexural frequency $f_B$; and wherein said resonant frequency $f_E$ is at least equal to said frequency $f_B$.

4. A system as set forth in claim 1, wherein said switch means comprises an electronic switch adapted to switch from a non-conductive to a conductive state in response to a switching signal; and wherein said means for creating said pulsed magnetic force further comprise means for furnishing said switching signal to said electronic switch.

5. A system as set forth in claim 4, wherein said electronic switch is a thyristor.

6. System for testing the bending resistance and damping of an individual tooth of a steel gear for detecting defects therein, comprising, in combination, means for creating a pulsed magnetic attractive force for bending said tooth and causing said tooth to execute free flexural vibrations; and sensing means positioned in operative proximity to said tooth for sensing said flexural vibrations and furnishing an electrical signal having a predetermined characteristic varying in correspondence thereto, wherein said sensor means comprise a contactless sensor for sensing the deflection of said tooth from a reference position as a function of time and furnishing an electrical signal corresponding thereto.

7. System for testing the bending resistance and damping of an individual tooth of a steel gear for detecting defects therein, comprising, in combination, means for creating a pulsed magnetic attractive force for bending said tooth and causing said tooth to execute free flexural vibrations; and sensing means positioned in operative proximity to said tooth for sensing said flexural vibrations and furnishing an electrical signal having a predetermined characteristic varying in correspondence thereto, wherein said sensor means comprise a contactless sensor for sensing the deflection as a function of time of said tooth from a reference position and furnishing an electrical signal corresponding to the derivative thereof.

8. System for texting the bending resistance and damping of an individual tooth of a steel gear for detecting defects therein, comprising, in combination, means for creating a pulsed magnetic attractive force for bending said tooth and causing said tooth to execute free flexural vibrations; and sensing means positioned in operative proximity to said tooth for sensing said flexural vibrations and furnishing an electrical signal having a predetermined characteristic varying in correspondence thereto, wherein said gear has at least one tooth adjacent to said tooth under test; further comprising a yoke for carrying said coil, the core of said coil and said sensor means, said yoke having at least one conforming surface contacting a surface of said adjacent tooth during the testing of said tooth under test.

9. A system as set forth in claim 8, wherein said yoke has a handle.

10. A system as set forth in claim 8, further comprising an automatic test fixture; wherein said yoke is part of said automatic test fixture; and wherein said automatic test fixture further comprises drive means for driving said yoke back and forth in a substantially radial direction relative to said gear while rotating said gear from one tooth to the next.

11. System for testing the bending resistance and damping of an individual tooth of a steel gear for detecting defects therein, comprising, in combination, means for creating a pulsed magnetic attractive force for bending said tooth and causing said tooth to execute free flexural bivations; and sensing means positioned in operative proximity to said tooth for sensing said flexural vibrations and furnishing an electrical signal having a predetermined characteristic varying in correspondence thereto, further comprising a source of electrical energy having a source frequency; and wherein said means for applying said switching signal to said electronic switch comprise means for furnishing said switching signal repeatedly at a frequency corresponding to said source frequency or an integral multiple or submultiple thereof.

12. System for testing the bending resistance and damping of an individual tooth of a steel gear for detecting defects therein, comprising, in combination, means for creating a pulsed magnetic attractive force for bending said tooth and causing said tooth to execute free flexural vibrations; and sensing means positioned in operative proximity to said tooth for sensing said flexural vibrations and furnishing an electrical signal having a predetermined characteristic varying in correspondence thereto, further comprising an oscilloscope having a time base generator for furnishing a deflection voltage varying as a linear function of time for a predetermined time interval following receipt of a trigger signal; wherein a decay time is associated with said flexural vibrations of said tooth; and wherein said predetermined time interval is less than approximately five times said decay time.

13. A method of testing the bending resistance and damping of an individual tooth of a steel gear in order to detect defects, comprising, in combination, the step of causing the tooth to perform free flexural vibrations of decaying amplitude by subjecting the tooth to shock excitation, the shock excitation being effected by applying to the tooth a single pulse of magnetic attractive force; and sensing the flexural vibrations and furnishing an electrical signal corresponding thereto.

14. The method defined in claim 13, the duration of the single pulse of magnetic attractive force being at most equal to one half the time period between successive cycles of the free flexural vibrations of the tooth.

15. The method defined in claim 13, the free flexural vibrations of the tooth decaying approximately exponentially with a time constant $T_A$, further comprising the step of repeating the shock excitation at intervals no shorter than $T_A$.

16. The method defined in claim 15, repeating the shock excitation at intervals no shorter than $5T_A$.

17. A system for testing the bending resistance and damping of an individual tooth of a steel gear for detecting defects in the tooth, comprising, in combination, means for causing the tooth to perform free flexural vibrations for decaying amplitude by subjecting the tooth to a shock excitation effected by applying to the tooth a single pulse of magnetic attractive force; and sensing means positioned in operative proximity to the tooth for sensing the free flexural vibrations and furnishing an electrical signal having a predetermined characteristic varying in correspondence thereto.

* * * * *